United States Patent

Aizawa et al.

[11] Patent Number: 6,163,757
[45] Date of Patent: Dec. 19, 2000

[54] METHOD OF AND APPARATUS FOR ANALYZING LINEAR OBJECT AND RECORDING MEDIUM HAVING LINEAR OBJECT ANALYZING PROGRAM STORED THEREON

[75] Inventors: Tatsuhiko Aizawa, Tokyo, Japan; Guilan Wang, Hubei, China; Junji Kihara, Tokyo, Japan; Sinji Kurashige, Tokyo, Japan; Takuya Murakami, Ibaraki, Japan

[73] Assignee: Tokyo Rope Mfg. Co., Ltd., Tokyo, Japan

[21] Appl. No.: 09/078,047

[22] Filed: May 13, 1998

[30] Foreign Application Priority Data

May 22, 1997 [JP] Japan .................................. 9-147047

[51] Int. Cl.[7] ...................................................... G01L 1/04
[52] U.S. Cl. ................................ 702/42; 702/43; 72/135; 72/183; 72/14.8
[58] Field of Search .................................. 702/42, 43, 73, 702/155, 156, 157, 158; 140/149, 71 R; 205/76; 73/78, 158, 160; 87/8; 156/167; 164/423; 57/200; 72/127, 135, 189, 183, 14.8; 29/527.5; 242/430

[56] References Cited

U.S. PATENT DOCUMENTS 4,283,955  8/1981  Nagy et al. ................................ 73/772
4,591,996  5/1986  Vachon .................................... 364/508

*Primary Examiner*—Marc S. Hoff
*Assistant Examiner*—Edward Raymond
*Attorney, Agent, or Firm*—Jordan and Hamburg LLP

[57] ABSTRACT

The characteristics of the wire are calculated, the wire having a cross-sectional shape which is substantially uniform along its length and having a length long enough in comparison with a diameter being deformed. The wire is divided into a plurality of elements with predetermined spacing along the length. When the wire is deformed, the shape of the wire after the deformation is determined. In the determined shape, a tangential stiffness equation using the element as a basis is calculated, and the calculated tangential stiffness equation is translated into a tangential stiffness equation using the whole of the wire as a basis. A global stiffness equation representing the whole wire is calculated from the tangential stiffness equation obtained by the translation. A load or a displacement produced in each portion of the wire is calculated from the global stiffness equation and the determined shape of the wire.

13 Claims, 15 Drawing Sheets

Fig. 14

| | |
|---|---|
| NUMBER OF ELEMENTS | 10 |
| NUMBER OF GAUSS' INTEGRAL POINTS | 6 |
| NUMBER OF NODAL POINTS OF ELEMENTS | 3 |
| YOUNG'S MODULAS COEFFICIENT | 183900 (MPa) |
| POISSON'S RATIO | 0.32 |
| YIELD STRESS | 744.8 (MPa) |
| WORK-HARDENING RATIO | 6069 |
| NUMBER OF SIDE WIRES (FILAMENTS) | 6 |
| ROPE LENGTH | 80 (mm) |
| ROPE DIAMETER | 8.50 (mm) |
| FILAMENT DIAMETER | 2.86 (mm) |
| ROPE PITCH | 150 (mm) |
| HERIX DIRECTION | LEFT |
| REVOLUTION RATE | 8.545132 |
| ROTATION RATE | 0.0 |
| INVERSE RATIO | 0 |

*Fig. 15*

| NODE NUMBER | X COORDINATE | Y COORDINATE | Z COORDINATE |
|---|---|---|---|
| 1 | 3.941 | 3.029 | 0.743 |
| 2 | 3.941 | 3.307 | 0.805 |
| 3 | 3.942 | 3.586 | 0.868 |
| 4 | 3.943 | 3.865 | 0.931 |
| 5 | 3.943 | 4.143 | 0.994 |
| 6 | 3.908 | 2.903 | 0.919 |
| 7 | 3.877 | 3.056 | 1.159 |
| 8 | 3.845 | 3.209 | 1.398 |
| 9 | 3.813 | 3.362 | 1.638 |
| 10 | 3.781 | 3.514 | 1.877 |
| 11 | 3.896 | 2.687 | 0.956 |
| 12 | 3.852 | 2.624 | 1.232 |
| 13 | 3.807 | 2.561 | 1.508 |
| 14 | 3.763 | 2.498 | 1.784 |
| 15 | 3.719 | 2.435 | 2.060 |
| 16 | 3.911 | 2.507 | 0.831 |
| 17 | 3.881 | 2.265 | 0.982 |
| 18 | 3.852 | 2.022 | 1.133 |
| 19 | 3.822 | 1.780 | 1.284 |
| 20 | 3.793 | 1.537 | 1.435 |
| 21 | 3.944 | 2.469 | 0.618 |
| 22 | 3.948 | 2.189 | 0.555 |
| 23 | 3.952 | 1.908 | 0.493 |
| 24 | 3.956 | 1.627 | 0.430 |
| 25 | 3.960 | 1.347 | 0.368 |
| 26 | 3.976 | 2.595 | 0.441 |
| 27 | 4.013 | 2.440 | 0.202 |
| 28 | 4.049 | 2.285 | -0.038 |
| 29 | 4.085 | 2.131 | -0.277 |
| 30 | 4.122 | 1.976 | -0.516 |
| 31 | 3.989 | 2.811 | 0.404 |
| 32 | 4.037 | 2.872 | 0.129 |
| 33 | 4.086 | 2.933 | -0.147 |
| 34 | 4.135 | 2.994 | -0.423 |
| 35 | 4.184 | 3.055 | -0.699 |
| 36 | 3.974 | 2.991 | 0.529 |
| 37 | 4.008 | 3.231 | 0.379 |
| 38 | 4.042 | 3.472 | 0.228 |
| 39 | 4.076 | 3.712 | 0.077 |
| 40 | 4.110 | 3.953 | -0.073 |
| 41 | 3.940 | 2.750 | 0.680 |

Fig. 16

| NODE NUMBER | NORMAL STRESS | SHEAR STRESS | EQUIVALENT STRESS | NORMAL STRAIN | SHEAR STRAIN | EQUIVALENT STRAIN |
|---|---|---|---|---|---|---|
| 1 | 116.03 | 284.57 | 506.37 | 0.00200 | 0.01500 | 0.01000 |
| 2 | 47.33 | 161.69 | 284.04 | 0.00500 | 0.03100 | 0.02400 |
| 3 | -27.99 | 39.92 | 74.59 | 0.00700 | 0.04600 | 0.03800 |
| 4 | -103.78 | -81.78 | 175.60 | 0.01000 | 0.06100 | 0.05100 |
| 5 | -178.93 | -202.25 | 393.35 | 0.01200 | 0.07600 | 0.06600 |
| 6 | 74.65 | 294.23 | 515.05 | 0.00200 | 0.01500 | 0.01000 |
| 7 | 30.77 | 172.49 | 300.34 | 0.00300 | 0.03100 | 0.02400 |
| 8 | -15.40 | 51.30 | 90.18 | 0.00500 | 0.04600 | 0.03700 |
| 9 | -61.13 | -69.93 | 135.68 | 0.00600 | 0.06100 | 0.05100 |
| 10 | -106.60 | -191.53 | 348.44 | 0.00800 | 0.07600 | 0.06500 |
| 11 | -17.38 | 299.76 | 519.50 | 0.00000 | 0.01500 | 0.01000 |
| 12 | -12.66 | 178.26 | 309.02 | 0.00000 | 0.03100 | 0.02300 |
| 13 | -3.21 | 57.07 | 98.89 | -0.00100 | 0.04600 | 0.03700 |
| 14 | 7.70 | -65.42 | 113.58 | -0.00100 | 0.06100 | 0.05100 |
| 15 | 19.11 | -187.23 | 324.86 | -0.00100 | 0.07600 | 0.06400 |
| 16 | -100.52 | 290.30 | 512.76 | -0.00200 | 0.01500 | 0.01000 |
| 17 | -49.47 | 166.96 | 293.38 | -0.00400 | 0.03100 | 0.02400 |
| 18 | 10.50 | 45.13 | 78.88 | -0.00600 | 0.04600 | 0.03700 |
| 19 | 71.78 | -76.50 | 150.70 | -0.00700 | 0.06100 | 0.05100 |
| 20 | 133.55 | -198.41 | 368.70 | -0.00900 | 0.07600 | 0.06500 |
| 21 | -125.46 | 284.68 | 508.79 | -0.00200 | 0.01500 | 0.01000 |
| 22 | -58.43 | 161.53 | 285.82 | -0.00500 | 0.03100 | 0.02400 |
| 23 | 16.74 | 39.73 | 70.82 | -0.00700 | 0.04600 | 0.03800 |
| 24 | 92.52 | -81.97 | 169.46 | -0.01000 | 0.06100 | 0.05100 |
| 25 | 167.66 | -202.43 | 388.64 | -0.01200 | 0.07600 | 0.06600 |
| 26 | -83.94 | 294.29 | 516.59 | -0.00200 | 0.01500 | 0.01000 |
| 27 | -41.89 | 172.37 | 301.47 | -0.00300 | 0.03100 | 0.02400 |
| 28 | 4.11 | 51.16 | 88.71 | -0.00500 | 0.04600 | 0.03700 |
| 29 | 49.81 | -70.07 | 131.19 | -0.00600 | 0.06100 | 0.05100 |
| 30 | 95.28 | -191.66 | 345.38 | -0.00800 | 0.07600 | 0.06500 |
| 31 | 8.20 | 299.76 | 519.27 | 0.00000 | 0.01500 | 0.01000 |
| 32 | 1.53 | 178.26 | 308.76 | 0.00000 | 0.03100 | 0.02300 |
| 33 | -8.13 | 57.07 | 99.18 | 0.00100 | 0.04600 | 0.03700 |
| 34 | -19.06 | -65.42 | 114.90 | 0.00100 | 0.06100 | 0.05100 |
| 35 | -30.48 | -187.23 | 325.73 | 0.00100 | 0.07600 | 0.06400 |
| 36 | 91.13 | 289.87 | 510.26 | 0.00200 | 0.01500 | 0.01000 |
| 37 | 38.35 | 167.07 | 291.91 | 0.00400 | 0.03100 | 0.02400 |
| 38 | -21.78 | 45.27 | 81.38 | 0.00600 | 0.04600 | 0.03800 |
| 39 | -83.09 | -76.36 | 156.20 | 0.00700 | 0.06100 | 0.05100 |
| 40 | -144.85 | -198.27 | 372.72 | 0.00900 | 0.07600 | 0.06500 |
| 41 | 0.00 | 0.00 | 0.00 | 0.00000 | 0.00000 | 0.00000 |

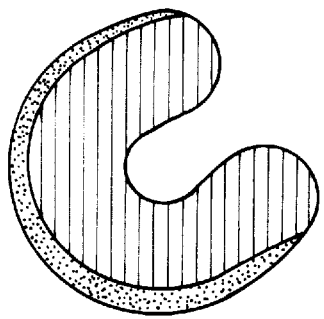
Fig.20a
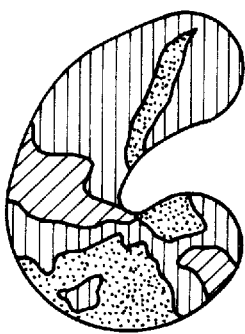
Fig.20b
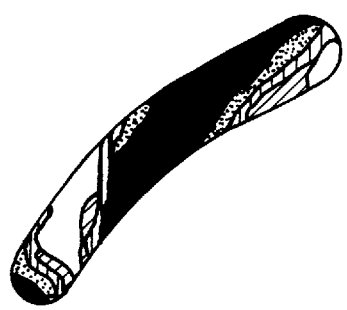
Fig.20c
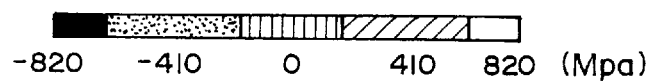
-820  -410  0  410  820 (Mpa)
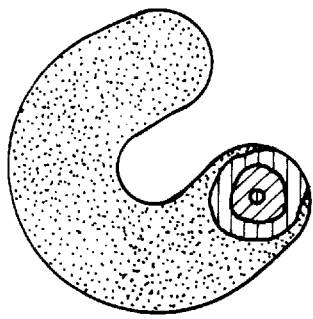
Fig.21a
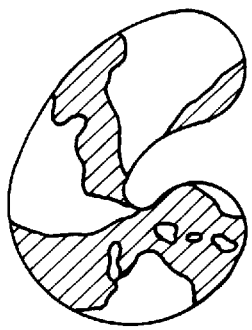
Fig.21b
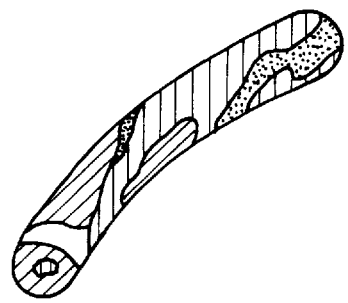
Fig.21c
-400  -200  0  200  400 (Mpa)

METHOD OF AND APPARATUS FOR ANALYZING LINEAR OBJECT AND RECORDING MEDIUM HAVING LINEAR OBJECT ANALYZING PROGRAM STORED THEREON

BACKGROUND OF THE INVENTION

1. Field of the Invention

The present invention relates to a method of and an apparatus for calculating at least one of a displacement and a load produced in each portion of a linear object, when the linear object is deformed, the linear object having a cross-section which is substantiously uniform along its length and having a length long enough in comparison with the diameter, as represented by a wire (elementary wire or single wire) constituting a wire rope, and a recording medium having a program for calculating the displacement stored thereon.

2. Related Art

A wire rope is utilized in a variety of fields such as construction equipment like cranes, elevators and cableways because it exhibits high flexibility and high strength. A lot of types of wire ropes, for example, a Seale type rope, a rope with filler wires and a Warrington Seale type rope which are constructed by complicated combinations of wires, in addition to a simple seven wire strand, are selected depending on the field of utilization.

Characteristics required of the wire rope have been subdivided into high strength, fatigue-resisting characteristics, rotating properties and so forth as the field of utilization is thus enlarged. In order to satisfy the required characteristics, heretofore, the specification of the wire rope and a method of manufacturing the wire rope have been determined mainly by experience, and field testing has been repeated.

In such a method, however, development and improvement in the wire rope takes long, and the cost of the wire rope rises.

SUMMARY OF THE INVENTION

An object of the present invention is to calculate, the characteristics (displacement, load, stress, strain, etc.) of a linear object which appear when the linear object is deformed, the linear object having a cross-section which is substantially uniform along its length and having a length long enough in comparison with the diameter, as represented by a wire constituting a wire rope.

The present invention utilizes a finite-element method.

When the finite-element method is utilized in a case where a linear object which is represented by a wire rope is deformed such that it is wound around a core wire, for example, the following points must be considered.

The first point is that it is a stranded wire forming process from a single wire (individual wire) to multiple wires (complex wires) of the linear object, for example, a high strength wire. The second point is that the linear object is formed by elasto-plastic deformation response because the inside of a cross section of the linear object is partially a plastic area, thereby necessitating analysis according to a finite deformation elasto-plastic finite element method (FEM). The third point is that the geometrical shape of the linear object is changed, followed by large rotation of a member, in a stranded wire forming process, thereby bringing about the necessity of considering rigid-body rotation accompanying no deformation of the linear object. The fourth point is that the linear object is subjected to extensional deformation, bending deformation and torsional deformation in a stranded wire forming process, thereby bringing about the necessity of considering and evaluating not only tensile-compressive (extensional) deformation of the linear object but also bending deformation and torsional deformation of the linear object.

On the other hand, in analysis according to a conventional finite deformation elasto-plastic finite element method considering the finite deformation, a suitable time increment is set, and a virtual work equation linearized per the time increment is solved, to calculate an incremental strain and an incremental stress. A strain and a stress after the time increment are determined using the calculated incremental strain and incremental stress. In this analysis, an approximate solution can be obtained in a deforming process in which an increment of rigid- body rotation per unit time is sufficiently small. In the stranded wire forming process of the linear object which is represented by a wire rope, however, the shape and the position of the linear object greatly vary by the deformation, so that the increment of rigid-body rotation per unit time is large enough in comparison with a strain per time produced by the deformation. A deformation velocity component caused by the rigid-body rotation is included in the amount of strain, so that the error significantly increases.

Therefore, it may, in some cases, be difficult to analyze a linear object having a length long enough in comparison with its diameter using the conventional finite deformation elasto-plastic finite element method.

The present invention has been made in consideration of the above-mentioned points.

A method of analyzing a linear object according to the present invention is characterized by comprising the steps of dividing a linear object having a cross-sectional shape which is substantially uniform along its length and having a length long enough in comparison with the diameter into a plurality of elements with predetermined spacing along the length, determining, when the linear object is deformed, a shape after the deformation, deriving for each of the elements a tangential stiffness equation in a local coordinate system using the element as a basis in the determined shape, translating the derived tangential stiffness equation for each of the elements in the local coordinate system into a tangential stiffness equation for each of the elements in a global coordinate system using the linear object as a basis, deriving a global stiffness equation for the whole of the linear object from the tangential stiffness equation for each of the elements in the global coordinate system which is obtained by the translation, and calculating at least one of the displacement of each of the elements and the load of each of the elements on the basis of the derived global stiffness equation for the whole linear object and the shape after the deformation.

The present invention also provides an apparatus suitable for carrying out the above-mentioned method. That is, the present invention provides an apparatus for analyzing a linear object, characterized by comprising setting means for performing such setting as to divide a linear object having a cross-sectional shape which is substantially uniform along its length and having a length long enough in comparison with the diameter into a plurality of elements with predetermined spacing along the length, shape determining means for determining, when the linear object is deformed, a shape after the deformation, stiffness equation deriving means for deriving for each of the elements, which are obtained by the setting in the setting means, a tangential stiffness equation for each of the elements in a local coordinate system using the element as a basis in the shape determined by the shape determining means, stiffness equation translating means for translating the tangential stiffness equation for each of the elements in the local coordinate system, which is derived by the stiffness equation deriving means, into a tangential stiffness equation for each of the elements in a global coordinate system using the linear object as a basis, global stiffness equation deriving means for deriving a global stiffness equation for the whole linear object from the tangential stiffness equation for each of the elements in the global coordinate system which is obtained by the translation in the stiffness equation translating means, and calculating means for calculating at least one of the displacement of each of the elements and the load of each of the elements on the basis of the global stiffness equation for the whole linear object which is derived by the global stiffness equation deriving means and the shape determined by the shape determining means.

Furthermore, the present invention also provides a recording medium having a program for carrying out the above-mentioned method stored thereon.

According to the present invention, the linear object is divided into a plurality of elements. Further, the local coordinate system using each of the elements as a basis and the global coordinate system using the linear object as a basis are introduced. The tangential stiffness equation for each of the elements in the local coordinate system is derived, and the derived tangential stiffness equation in the local coordinate system is translated into the tangential stiffness equation for each of the elements in the global coordinate system, to derive the global stiffness equation for the whole linear object. At least one of the displacement and the load of the element is calculated from the derived global stiffness equation. It is thus possible to calculate the characteristics of the linear object in a case where the linear object is deformed.

When the tangential stiffness equation for each of the elements in the local coordinate system is translated into the tangential stiffness equation for the element in the global coordinate system, rigid-body rotation of the element is distinguished from extensional deformation, bending deformation and torsional deformation of the element, so that the translation can be relatively accurately made.

The linear object shall be gradually deformed. Processing for deriving the tangential stiffness equation for each of the elements in the local coordinate system, translating the derived tangential stiffness equation for the element in the local coordinate system into the tangential stiffness equation for the element in the global coordinate system, deriving the global stiffness equation for the whole linear object, and calculating the displacement of the element is repeated until the linear object has a final shape.

When the displacement of each of the elements is calculated, a stress, a strain and so forth in the element can be calculated on the basis of the calculated displacement of the element.

The origin of the local coordinate system is taken at the center of the element, for example. Consequently, the translation processing is made relatively easy.

Furthermore, nodes in the element can be defined at both ends and the center on the central axis of the element.

BRIEF DESCRIPTION OF THE DRAWINGS

FIG. 14 shows input data in wire rope analysis;

FIGS. 15 and 16 show output data in wire rope analysis;

FIGS. 20a to 20c illustrate a residual normal stress in a case where a wire rope is unloaded; and FIGS. 21a to 21c illustrate a residual shear stress in a case where a wire rope is unloaded.

DESCRIPTION OF THE PREFERRED EMBODIMENT

I. Outline of Analysis of Filament

Figure 1:
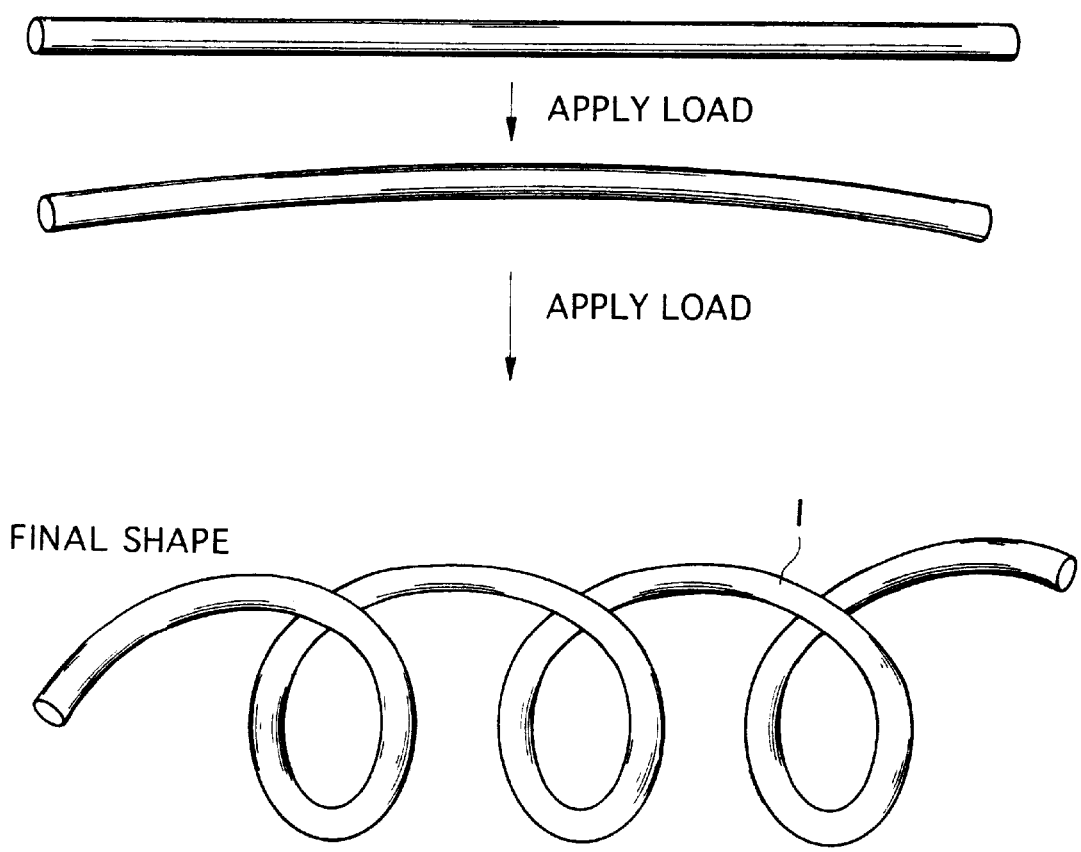
FIG. 1 shows states where a filament is being deformed.

In the present embodiment, a filament (inclusive of a wire) 1 is prepared, as shown in FIG. 1, to analyze, when the filament 1 is wound around a core wire (core filament)(not shown) upon being loaded to form a wire rope (strand), a load or a displacement produced in each portion of the filament 1. A final shape (form) of the filament 1 after loading has been completed has been previously found by known geometry analysis.

The filament 1 is a linear object having a cross section which is substantially uniform along its length and having a length long enough in comparison with the diameter.

The load is gradually applied to the filament 1, so that the filament 1 is gradually deformed into the final shape.

Figure 2:
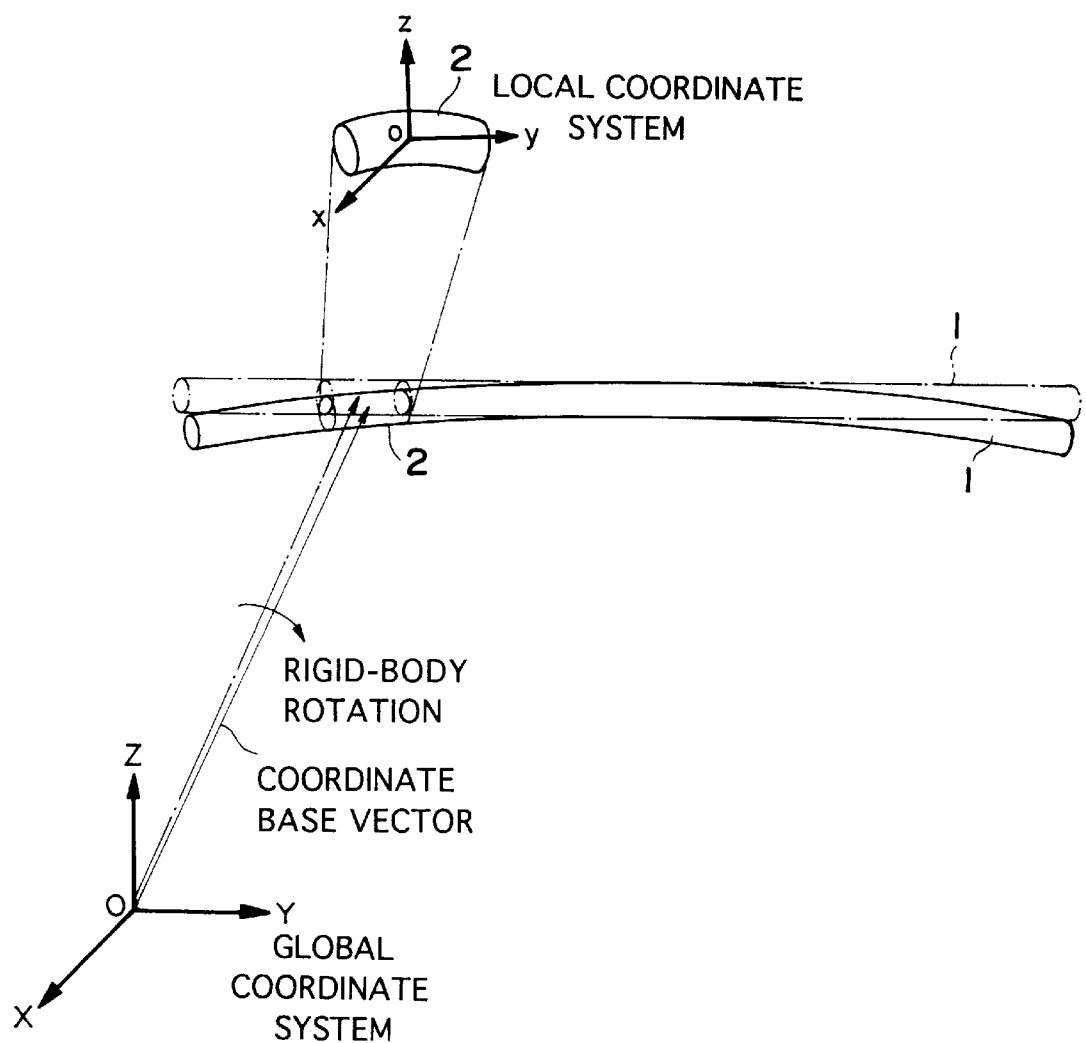
FIG. 2 illustrates the relation between a local coordinate system and a global coordinate system.

FIG. 2 shows the state in which the filament 1 is loaded. In FIG. 2, the filament 1 being loaded is indicated by a solid line, and the filament 1 in an initial shape (form) before loading is indicted by a one-dot and dash line. The filament 1 is divided into a plurality of elements 2 with predetermined spacing along the length. In FIG. 2, one element is typically illustrated.

A coordinate system using the whole of the filament 1 as a basis is taken as a global coordinate system XYZ, and a coordinate system using the element 2 as a basis is taken as a local coordinate system xyz. In the global coordinate system XYZ, a vector representing the position of the element 2 is called a coordinate base vector.

Figure 3:
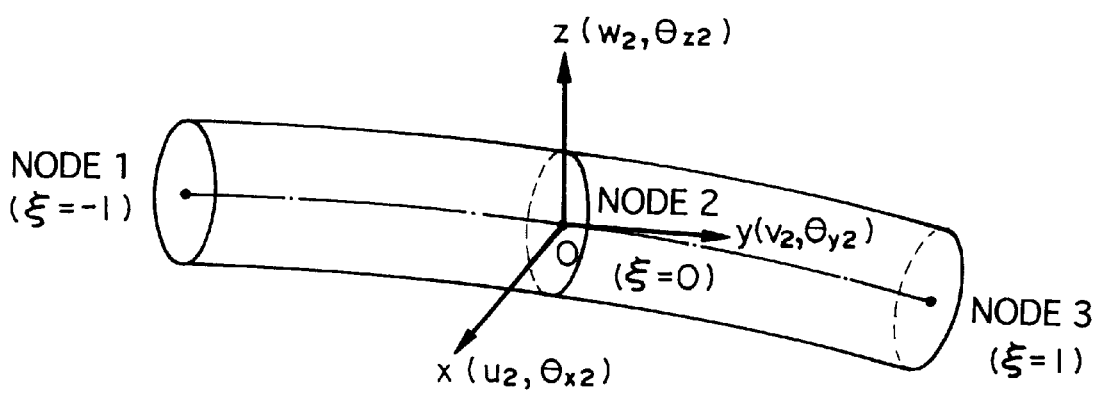
FIG. 3 illustrates an element with it being taken out.

FIG. 3 illustrates a state where the filament 1 is loaded, so that the element 2 is subjected to laid (twisted) deformation.

In the element 2, three nodes, that is, a node 1, a node 2 and a node 3 are defined. The node 1 and the node 3 are respectively defined at central positions on both end faces of the element 2. The node 2 is defined at the center of a central cross section of the element 2. The node 2 coincides with the origin of the local coordinate system xyz.

When the filament 1 is loaded, the filament 1 is laid, so that the element 2 constituting the filament 1 is also subjected to laid deformation. The laying of the element 2 is analyzed into displacements along respective axes and a torsional angular displacements around respective axes in the local coordinate system xyz. In the example shown in FIG. 3, the element 2 is laid, so that the node 2 is displaced by $u_2$ in the x direction, displaced by $v_2$ in the y direction, and is displaced by $w_2$ in the z direction in the local coordinate system xyz. Further the node 2 in the element 2 is displaced through an angle of $\theta_{x2}$ around the x axis, displaced through an angle of $\theta_{y2}$ around the y axis, and displaced through an angle of $\theta_{z2}$ around the z axis in the local coordinate system xyz.

In the analysis of the load or the displacement of the filament 1 in the present embodiment, a finite-element method is utilized.

When deformation of the linear object such as the filament 1 is analyzed utilizing the finite-element method, it is necessary to carry out finite-element elasto-plasticity analysis, as described above, consider rigid-body rotation accompanying no deformation of the filament 1, and further consider bending deformation and torsional deformation of the filament 1.

In order to perform analysis taking rigid-body rotation into consideration, a geometric shape which greatly changes per time increment shall be represented in the form of mapping, to handle space rotational motion with high precision. This is accomplished by representing a coordinate base vector as the product of a rotational transformation matrix T and a coordinate base vector E0 before the increment. Rigid-body rotation from a coordinate base vector before an increment to a coordinate base vector after an arbitrary increment can be relatively strictly handled by the above coordinate representation. Letting E be a coordinate base vector after the increment, and letting E0 be a coordinate base vector before the increment, the following equation is obtained:

$$E = T \cdot E0 \qquad \text{Eq. 1}$$

Letting $\theta$ be an axial vector, and letting S be a spin matrix appended to the axial vector $\theta$, the rotational transformation vector T is expressed by the following equation:

$$T = I + (\sin\theta/\theta)S + (1-\cos\theta)/\theta^2 \cdot S^2 \qquad \text{Eq. 2}$$

Furthermore, in order to consider bending deformation and extensional deformation of the filament 1, the local coordinate system xyz is introduced for each element 2, a displacement along the length of the filament 1 which causes extension and torsion are subjected to Hermitian interpolation by a quadratic equation, and a displacement along each axis which is to be bending is subjected to Hermitian interpolation by a 5-th order equation.

Since the bending and the extensional displacement of the element 2 are handled separately from a displacement produced by the rigid-body rotation, the local coordinate system xyz can be relatively accurately translated into the global coordinate system XYZ.

In the present embodiment, a tangential stiffness equation for the element 2 in the local coordinate system xyz is first introduced upon defining the global coordinate system XYZ and the local coordinate system xyz. Second, the introduced tangential stiffness equation for the element 2 is translated into a tangential stiffness equation for the element 2 in the global coordinate system XYZ. Third, a global stiffness equation in the global coordinate system XYZ is derived from the tangential stiffness equation for each element 2 in the global coordinate system XYZ which is obtained by the translation. A stress and a strain produced in the element 2 are found from the calculated global stiffness equation in the global coordinate system In the translation of the tangential stiffness equation in the local coordinate system into the tangential stiffness equation in the global coordinate system which will be performed in the second stage, rigid-body rotation accompanying no deformation of the filament 1 is separated, as described later, from bending deformation and extensional deformation of the filament 1. According to the present embodiment, it is relatively accurately feasible to make analysis utilizing the finite-element method in a case where the filament 1 is deformed.

(1) Derivation of tangential stiffness equation for each element in local coordinate system Description is now made of the step of deriving a tangential stiffness equation for each element 2 in the local coordinate system xyz.

When the filament 1 is loaded, the following Eq. 3 is minimized based on a theorem of minimal potential energy (potential energy introduced from a displacement satisfying a differential equation of equilibrium in a body is smaller than potential energy introduced by any other displacement satisfying the same conditions on a boundary surface):

$$\pi(\epsilon^*) = \tfrac{1}{2} \int_\Omega \epsilon^{*t} \sigma^* dv - \int_{ST}(V^*)^t T ds - \int_\Omega (F_V)^t V dv \qquad \text{Eq. 3}$$

where $v^*$: displacement rate vector $\epsilon^*$: strain velocity vector

T: force rate in known stress boundary

F: bulk force rate

In the Eq. 3, the left side represents potential energy, the first term in the right side represents strain energy, the second term in the right side represents an amount of work by a body force, and the third term in the right side represents an amount of work by a surface force. A transposed matrix is marked with t at the upper right of the character.

The Eq. 3 can be transformed into the following Eq. 4, considering that a general constitutive equation is expressed such that a stress velocity is equal to the product of a stiffness matrix and a strain velocity, a force rate vector of the element 2 is constituted by six components, that is, three axial forces of the three axes and three moments around the three axes, and a displacement rate vector of the element 2 is constituted by six components, that is, three axial displacements along the three axes and three torsional angles around the three axes as seen from the definition of the element 2, and a B matrix of the element 2 is used:

$$\pi^e(\epsilon^t) = \tfrac{1}{2} V^{*et} [\int_{\Omega e} B^t D B d\Omega] V^{*e} - V^{*et} F \qquad \text{Eq. 4}$$

The mark e at the upper right of the character indicates that it is related to the element 2.

In the Eq. 4, $v^{*et}$ is expressed by the following equation:

$$V^{*et} = (u^{et}, v^{et}, w^{et}, \theta_y{}^t, \theta_z{}^t, \theta_x{}^t) \qquad \text{Eq. 5}$$

F is expressed by the following equation:

$$F = (n_x{}^t, n_y{}^t, n_z{}^t, m_y, m_z, m_x) \qquad \text{Eq. 6}$$

where $m_x$, $m_y$ and $m_z$ are respectively node moment vectors in the x direction, the y direction and the z direction, and $n_x$, $n_y$ and $n_z$ are respectively vectors representing node forces (excluding moments) in the x direction, the y direction and the z direction.

The conditions under which the potential energy of the element 2 is minimized is that a variational function of the potential energy with respect to a strain velocity vector takes a value of zero. Accordingly, Eq. 4 can be deformed into the following Eq. 7:

$$[\int_{\Omega e} B^t D \, B \, d\Omega](u \; v \; w \; \theta_y \theta_z \theta_x)^t = (n_x n_y n_z m_y m_z m_x)^t \quad \text{Eq. 7}$$

B is called a B matrix, and D is called a D matrix (an element stiffness matrix $D^e$ in an elastic state or an element stiffness matrix $D^P$ in a plastic state).

$K^e$ is a stiffness matrix of the element 2, $\delta d^e$ is a displacement vector of the element 2, and $\delta F^e$ is a vector representing a stress in the element 2.

The Eq. 7 can be expressed by the following Eq. 8:

$$K^e \delta d^e = \delta F^e \quad \text{Eq. 8}$$

The Eq. 7 (Eq. 8) is a tangential stiffness equation for each element 2 in the local coordinate system xyz which is to be first found.

(2) Translation of local coordinate system into global coordinate system

When the tangential stiffness equation for each element 2 in the local coordinate system xyz is derived, the tangential stiffness equation is translated into a tangential stiffness equation for the element 2 in the global coordinate system XYZ.

The translation will be described.

Nodes and the inside of the element 2 are related to each other, and nodes in the elements and the whole of the filament 1 are then related to each other, to translate the tangential stiffness equation for each element 2 in the local coordinate system xyz into a tangential stiffness equation for the element 2 in the global coordinate system XYZ.

(i) Relation between nodes and inside of element

The B matrix, the element stiffness matrix $D^e$ in an elastic state, and the element stiffness matrix $D^P$ in a plastic state are calculated.

The B matrix is calculated as follows.

An interpolation function for interpolating a displacement which are to be extension along the length of the element 2 and torsion with a quadratic equation is first defined by the following Eq. 9:

$$N_1 = -\frac{1}{2}\xi(1 - \xi) \quad \text{Eq. 9}$$
$$N_2 = (1 - \xi)(1 + \xi)$$
$$N_3 = \frac{1}{2}\xi(1 + \xi)$$

Furthermore, an interpolation function for interpolating displacements in two directions perpendicular to the axial direction which is to be bending in the element 2 with a 5-th order equation is defined by the following Eq. 10:

$$N_{v1} = \frac{1}{4}\xi^2(1 - \xi)^2(4 + 3\xi) \quad \text{Eq. 10}$$
$$N_{v2} = (1 - \xi)^2(1 + \xi)^2$$
$$N_{v3} = \frac{1}{4}\xi^2(1 + \xi)^2(4 - 3\xi)$$
$$N_{\theta 1} = \frac{L}{8}\xi^2(1 - \xi)^2(1 + \xi)$$
$$N_{\theta 2} = \frac{L}{2}\xi(1 - \xi)^2(1 + \xi^2)$$

-continued
$$N_{\theta 3} = -\frac{L}{8}\xi^2(1 + \xi)^2(1 - \xi)$$

In the Eqs. 9 and 10, $\xi$ is expressed by the following Eq. 11, where x is arbitrary positional coordinates inside the element 2, and L is the length of the element 2:

$$\xi = \frac{2x^e}{L} \quad \text{Eq. 11}$$

A displacement u in the x direction and a torsional angle in the arbitrary coordinates inside the element 2 are calculated by the following Eq. 12 with reference to the Eqs. 9 and 10:

$$u^e = N_1 u_1^e + N_2 u_2^e + N_3 u_3^e$$
$$\theta_x = N_1 \theta_{x1}^e + N_2 \theta_{x2}^e + N_3 \theta_{x3}^e \quad \text{Eq. 12}$$

where $u_1^e$ is a displacement in the x direction at the node 1, $\theta_{x1}^e$ is a torsional angle at the node 1, $\theta_{ex}^2$ is a torsional angle at the node 2, and $\theta_{x3}^e$ is a torsional angle at the node 3.

A displacement in the y direction and a displacement in the z direction in the arbitrary coordinates inside the element 2 are calculated by the following Eqs. 13 and 14 with reference to the Eqs. 9 and 10:

$$v^e = N_{v1}v_1^e + N_{\theta 1}\theta_{z1}^e + N_{v2}v_2^e + N_{\theta 2}\theta_{z2}^e + N_{v3}v_3^e + N_{\theta 3}\theta_{z3}^e \quad \text{Eq. 13}$$

$$w^e = N_{v1}w_1^e - N_{\theta 1}\theta_{y1}^e + N_{v2}w_2^e - N_{\theta 2}\theta_{y2}^e + N_{v3}w_3^e - N_{\theta 3}\theta_{y3}^e \quad \text{Eq. 14}$$

As can be seen from FIG. 3, a torsional angle $\theta_y$ in the y direction and a torsional angle $\theta_z$ in the z direction in the arbitrary coordinates inside the element 2 are neglected because they are very small.

In the Eqs. 10 to 12, the displacement $u^e$ in the x direction, a displacement $v^e$ in the y direction, and a displacement $w^e$ in the z direction are calculated in consideration of extensional deformation and bending deformation ($u_1^e$, $u_2^e$, $u_3^e$, $v_1^e$, $v_2^e$, $v_3^e$, $w_1^e$, $w_2^e$, $w_3^e$) and torsional deformation ($\theta_{x1}^e$, $\theta_{x2}^e$, $\theta_{x3}^e$, $\theta_{y1}^e$, $\theta_{y2}^e$, $\theta_{y3}^e$, $\theta_{z1}^e$, $\theta_{z2}^e$, $\theta_{z3}^e$), so that the tangential stiffness equation in the local coordinate system xyz can be relatively accurately translated into the tangential stiffness equation in the global coordinate system XYZ.

On the other hand, a strain and a displacement in the local coordinate system are related to each other as follows.

A strain $\epsilon_{xt}$ due to extensional deformation in the axial direction is expressed by the following Eq. 15:

$$\varepsilon_{xt} = \frac{du}{dx} \quad \text{Eq. 15}$$

A strain $K_x$ due to torsional deformation in the axial direction is expressed by the following Eq. 16:

$$K_x = \frac{d\theta_y}{dx} \quad \text{Eq. 16}$$

Bending deformation curvatures $K_y$ and $K_z$ in a plane including axes are expressed by the following Eq. 17 in an xoz plane, while being expressed by the following Eq. 18 in an xoy plane:

$$K_y = \frac{d^2 w}{dx^2} \qquad \text{Eq. 17}$$

$$K_z = \frac{d^2 v}{dx^2} \qquad \text{Eq. 18}$$

where $$N_x = (N_1, N_2, N_3)^t \qquad \text{Eq. 19}$$
$$N_v = (N_{v1}, N_{v2}, N_{v3})^t$$
$$N_\theta = (N_{\theta 1}, N_{\theta 2}, N_{\theta 3})^t$$

$$u = (u_1, u_2, u_3)^t \qquad \text{Eq. 20}$$
$$v = (v_1, v_2, v_3)^t$$
$$w = (w_1, w_2, w_3)^t$$
$$\theta_x = (\theta_{x1}, \theta_{x2}, \theta_{x3})^t$$
$$\theta_y = (\theta_{y1}, \theta_{y2}, \theta_{y3})^t$$
$$\theta_z = (\theta_{z1}, \theta_{z2}, \theta_{z3})^t$$

Furthermore, the following equations are calculated:

$$N_{x,x} = \frac{dN_x}{dx} = -\frac{1}{L}\begin{Bmatrix} 1 - 2\xi \\ 4\xi \\ 1 + 2\xi \end{Bmatrix} \qquad \text{Eq. 21}$$

$$N_{v,x} = \frac{dN_x}{dx} = \frac{1}{2L}\begin{Bmatrix} \xi(1-\xi)(8 - 7\xi - 15\xi^2) \\ -16\xi(1+\xi)(1-\xi) \\ \xi(1+\xi)(8 + 7\xi - 15\xi^2) \end{Bmatrix} \qquad \text{Eq. 22}$$

$$N_{\theta,x} = \frac{dN_\theta}{dx} = \frac{1}{4}\begin{Bmatrix} \xi(1-\xi)(2 - \xi - 5\xi^2) \\ 4(1 - 5\xi^4) \\ -\xi(1+\xi)(2 + \xi - 5\xi^2) \end{Bmatrix} \qquad \text{Eq. 23}$$

$$(N_{v,x})_x = \frac{d^2 N_v}{dx^2} = \frac{2}{L^2}\begin{Bmatrix} 4 - 15\xi - 12\xi^2 + 30\xi^3 \\ -16(1 - \xi - \xi^2) \\ 4 + 15\xi - 12\xi^2 - 30\xi^3 \end{Bmatrix} \qquad \text{Eq. 24}$$

$$(N_{\theta,x})_x = \frac{d^2 N_\theta}{dx^2} = -\frac{1}{L}\begin{Bmatrix} -1 + 3\xi + 6\xi^2 - 10\xi^3 \\ 40\xi^3 \\ 1 + 3\xi - 6\xi^2 - 10\xi^3 \end{Bmatrix} \qquad \text{Eq. 25}$$

A tensile strain $\epsilon_x$ in the axial direction is expressed by the following Eq. 26:

$$\epsilon_x = \epsilon_{xt} + \epsilon_{by} + \epsilon_{bz} = \epsilon_{xt} - zK_y + yK_z \qquad \text{Eq. 26}$$

A shear strain $\gamma$ due to torsional deformation in the axial direction is expressed by the following Eq. 27:

$$\gamma = \sqrt{y^2 + z^2} K_x = \gamma K_x \qquad \text{Eq. 27}$$

When the Eqs. 12 to 25 are substituted in the Eqs. 26 and 27 and are rearranged, the following Eq. 28 is obtained:

$$\begin{pmatrix} \epsilon_x \\ \gamma \end{pmatrix} = \qquad \text{Eq. 28}$$

$$\begin{bmatrix} N_{x,x}^t, & y(N_{v,x})_x^t, & z(N_{v,x}^t)_x, & -z(N_{\theta,x}^t)_x, & y(N_{\theta,x}^t)_x, & 0 \\ 0, & 0, & 0, & 0, & 0, & \gamma N_{x,x}^t \end{bmatrix} \begin{pmatrix} u \\ v \\ w \\ \theta_y \\ \theta_z \\ \theta_x \end{pmatrix}$$

The Eq. 28 can be expressed by the following Eq. 29:

$$\epsilon^e = B\, d^e \qquad \text{Eq. 29}$$

The B matrix can be expressed by the following Eq. 30 with reference to the Eqs. 28 and 29:

$$B = \begin{bmatrix} N_{x,x}^t, & y(N_{v,x})_x^t, & z(N_{v,x}^t)_x, & -z(N_{\theta,x}^t)_x, & y(N_{\theta,x}^t)_x, & 0 \\ 0, & 0, & 0, & 0, & 0, & \gamma N_{x,x}^t \end{bmatrix} \qquad \text{Eq. 30}$$

Next, the element stiffness matrix $D^e$ in an elastic state and the element stiffness matrix $D^p$ in a plastic state are calculated.

A stiffness matrix $K_t$ by an extensional displacement is first calculated.

Since a stress is equal to the product of a strain in the axial direction and a longitudinal elastic coefficient matrix, the stiffness matrix $K_t$ is expressed by the following Eq. 31, assuming $S_o$ be the cross-sectional area of the element 2:

$$K_t = S_o E \left( \int_{-x}^{x} N_{x,x}(N_{x,x})^t \, dx \right) \qquad \text{Eq. 31}$$

A stiffness matrix $K_{bx}$ by a bending displacement in the xoy plane is then calculated.

Letting $J_z$ be a 2nd-order sectional moment with respect to the z axis of the element 2, and letting E be a longitudinal elastic coefficient, the stiffness matrix $K_{bz}$ is expressed by the following Eq. 32:

$$K_{bz} = EJ_z \int ((N_{v,x})_x (N_{\theta,x})_x)^t ((N_{v,x}^t)_x (N_{\theta,x}^t)_x) dx \qquad \text{Eq. 32}$$

A stiffness matrix $K_{by}$ by a bending displacement in the xoz plane is then calculated.

Letting $J_y$ be a 2nd-order sectional moment with respect to the y axis of the element 2, the stiffness matrix $K_{by}$ is expressed by the following Eq. 33:

$$K_{by} = EJ_y \int ((N_{v,x}) - (N_{\theta,x})_x)^t ((N_{v,x}^t)_x - (N_{\theta,x}^t)_x) dx \qquad \text{Eq. 33}$$

Furthermore, a stiffness matrix $K_{tor}$ by a torsional displacement is further calculated.

Since a shear stress is found by the inner product of a shear strain and a shear modulus of elasticity (transverse elastic coefficient), the stiffness matrix $K_{tor}$ is expressed by the following Eq. 34, where K is a torsion constant of Sant-Venant, and G is a shear modulus of elasticity:

$$K_{Tor} = GK \int N_{x,x} N_{x,x}^t dx \qquad \text{Eq. 34}$$

In the Eqs. 31 to 34, the integration is performed by numerical integration, thereby obtaining a constant coefficient. Further, considering that the constant coefficient obtained by the numerical integration is generally omitted, the element stiffness matrix De in an elastic state is obtained as the following Eq. 35 using the stiffness matrices $K_t$, $K_{bz}$, $K_{by}$ and $K_{tor}$ expressed by the Eqs. 31, 32, 33 and 34:

$$D^e = \begin{bmatrix} ES_o & 0 & 0 & 0 \\ 0 & GK & 0 & 0 \\ 0 & 0 & EJ_y & 0 \\ 0 & 0 & 0 & EJ_z \end{bmatrix} \quad \text{Eq. 35}$$

The element stiffness matrix $D^P$ in a plastic state is obtained from the following Eq. 36, where f is a plastic potential:

$$D^p = D^e - \frac{D^e(\partial f/\partial \sigma)(\partial f/\partial \sigma)^t D^e}{(H/A) + (\partial f/\partial \sigma)^t D^e(\partial f/\partial \sigma)} \quad \text{Eq. 36}$$

The plastic potential f is expressed by the following Eq. 37 in terms of generalized stresses $\{N_1, M_x, M_y, M_z\}$ and generalized strains $\{\epsilon_x, \epsilon_x, K_y, K_z\}$ on the basis of the condition of Levy-Mises. Where, $w_{co,i}$ (i is x, y or z) is an elasto-plastic sectional coefficient found from the yield condition of a simple load, E is a Young's modulus (longitudinal elastic coefficient), H is a work-hardening ratio, $\gamma$ is the ratio of the area of an elastic area to the area of a plastic area.

$$f^2 = \left(\frac{N}{A}\right)^2 + 3\left(\frac{M_x}{w_{co,x}}\right)^2 + \left(\frac{M_y}{w_{co,y}}\right)^2 + \left(\frac{M_z}{w_{co,z}}\right)^2 + \frac{2\gamma N}{A}\sqrt{\left(\frac{M_y}{w_{co,y}}\right)^2 + \left(\frac{M_z}{w_{co,z}}\right)^2} \quad \text{Eq. 37}$$

(ii) Relation between nodes in elements and whole of filament

Nodes in the elements and the whole of the filament are then related to each other.

Since the amount of work owing to a stress does not depend on a coordinates system, the amounts of work for the element 2 are the same irrespective of whether it is represented in the local coordinate system xyz or in the global coordinate system XYZ in the present embodiment. From the foregoing, the following Eq. 38 holds, where g positioned at the right upper of the character represents the global coordinate system:

$$\delta d^{et}F^e = \delta d^{gt}F^g \quad \text{Eq. 38}$$

F in the Eq. 38 is a generalized stress, and is constituted by six components, that is, axial forces in the x, y and z directions and moments around the x, y and z axes, as expressed by the following Eq. 39:

$$F^g = (n_1{}^{gt}\ m_1{}^{gt}\ n_2{}^{gt}\ m_2{}^{gt}\ n_3{}^{gt}\ m_3{}^{gt})^t \quad \text{Eq. 39}$$

When the filament 1 is laid, the element 2 is loaded due to the laying of the filament 1, thereby not only deforming the element 2 itself but also causing rotation and translation (rigid displacement) of the element 2 accompanying no deformation of the element 2.

When the tangential stiffness equation for each element in the local coordinate system xyz is translated into the tangential stiffness equation for the element 2 in the global coordinate system XYZ, the rigid displacement of the element 2 must be considered.

When the rigid displacement is considered, the relation between a displacement vector in the tangential stiffness equation for each element 2 in the local coordinate system xyz and a displacement vector in the tangential stiffness equation for the element 2 in the global coordinate system XYZ can be expressed by the following Eq. 40:

$$\delta d^e = (H^t G^t A - P)\delta d^g \quad \text{Eq. 40}$$

The relation between a tangential stiffness matrix $K^e$ for each element 2 in the local coordinate system xyz and a tangential stiffness matrix $K_T$ for the element 2 in the global coordinate system XYZ is expressed by the following Eq. 41 using the Eq. 40:

$$K_T = [G\ K^e(G^t A - H\ P) - Q]M \quad \text{Eq. 41}$$

In the Eq. 41, A, H, M, G, and Q are respectively expressed by the following Eqs. 42, 43, 44, 45, and 46 to 48:

$$A = \begin{bmatrix} I & 0 & 0 & spin(EX_1^e) & 0 & 0 \\ 0 & I & 0 & -I & 0 & 0 \\ 0 & 0 & I & spin(EX_2^e) & 0 & 0 \\ 0 & 0 & 0 & 0 & 0 & 0 \\ 0 & 0 & 0 & spin(EX_3^e) & I & 0 \\ 0 & 0 & 0 & -I & 0 & I \end{bmatrix} \quad \text{Eq. 42}$$

where I is an identity transformation matrix, E is a base coordinate vector, $X_1^e$, $X_2^e$ and $X_3^e$ are the respective x coordinates of the nodes 1, 2 and 3 in the local coordinate system, and Spin is a row rotational vector:

$$H = \begin{bmatrix} I & 0 & 0 & 0 & 0 & 0 \\ 0 & T_1^e & 0 & 0 & 0 & 0 \\ 0 & 0 & I & 0 & 0 & 0 \\ 0 & 0 & 0 & T_2^e & 0 & 0 \\ 0 & 0 & 0 & 0 & I & 0 \\ 0 & 0 & 0 & 0 & 0 & T_3^e \end{bmatrix} \quad \text{Eq. 43}$$

where $T_1^e$, $T_2^e$ and $T_3^e$ are rotational transformation matrices of the nodes 1, 2 and 3 for the element 2.

$$M = \begin{bmatrix} I & 0 & 0 & 0 & 0 & 0 \\ 0 & E & 0 & 0 & 0 & 0 \\ 0 & 0 & I & 0 & 0 & 0 \\ 0 & 0 & 0 & E & 0 & 0 \\ 0 & 0 & 0 & 0 & I & 0 \\ 0 & 0 & 0 & 0 & 0 & E \end{bmatrix} \quad \text{Eq. 44}$$

$$G = diag(E) \quad \text{Eq. 45}$$

$$Q = F\ \Gamma \quad \text{Eq. 46}$$

$$\Gamma = [0\ 0\ 0\ I\ 0\ 0] \quad \text{Eq. 47}$$

$$F = \begin{bmatrix} spin(En_1^c) \\ spin(Em_1^c) \\ spin(En_2^c) \\ spin(Em_2^c) \\ spin(En_3^c) \\ spin(Em_3^c) \end{bmatrix} \quad \text{Eq. 48}$$

The Eqs. 38, 40 and 41 obtained in the foregoing manner are substituted in the Eq. 8 and are rearranged, a tangential stiffness equation for each element 2 in the global coordinate system XYZ is obtained, as expressed by the following Eq. 49:

$$\delta f^g = K_t \delta d^g \quad \text{Eq. 49}$$

(3) Calculation of global stiffness equation

When the tangential stiffness equation for each element 2 in the global coordinate system XYZ is obtained, as expressed by the Eq. 49, all the equations for elements 2 of the filament 1 are superimposed with each other for each node, so that a global stiffness equation for the filament 1 after being loaded is calculated. The global stiffness equation is expressed by the following Eq. 50:

$$\left\{ \sum_{e=1}^{E} [K^g]_e \right\} \delta P = \delta Q \quad \text{Eq. 50}$$

In the Eq. 50, one of a displacement increment vector $\delta P$ or a total node force vector $\delta Q$ is previously found by analyzing the shape of the filament 1 after being loaded, so that the unknown other of the displacement increment vector $\delta P$ and the total node force vector $\delta Q$ can be calculated from the global stiffness equation.

By repeating the above-mentioned method more than one to several hundred times, the filament can be analyzed from the initial shape to the final shape.

II Processing in laying step of filament 1

(1) Apparatus for analyzing linear object

Figure 4:
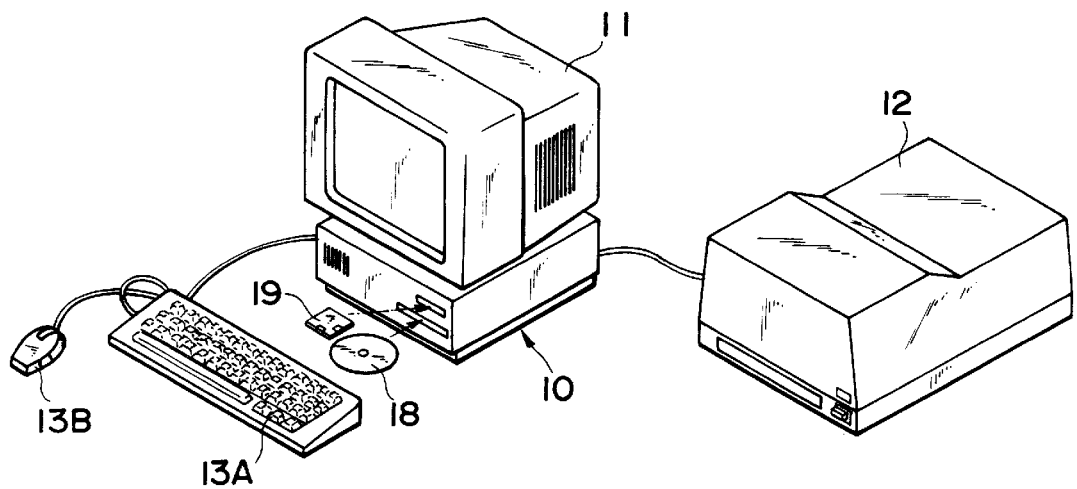
FIG. 4 illustrates the appearance of an apparatus for analyzing a filament.
Figure 5:
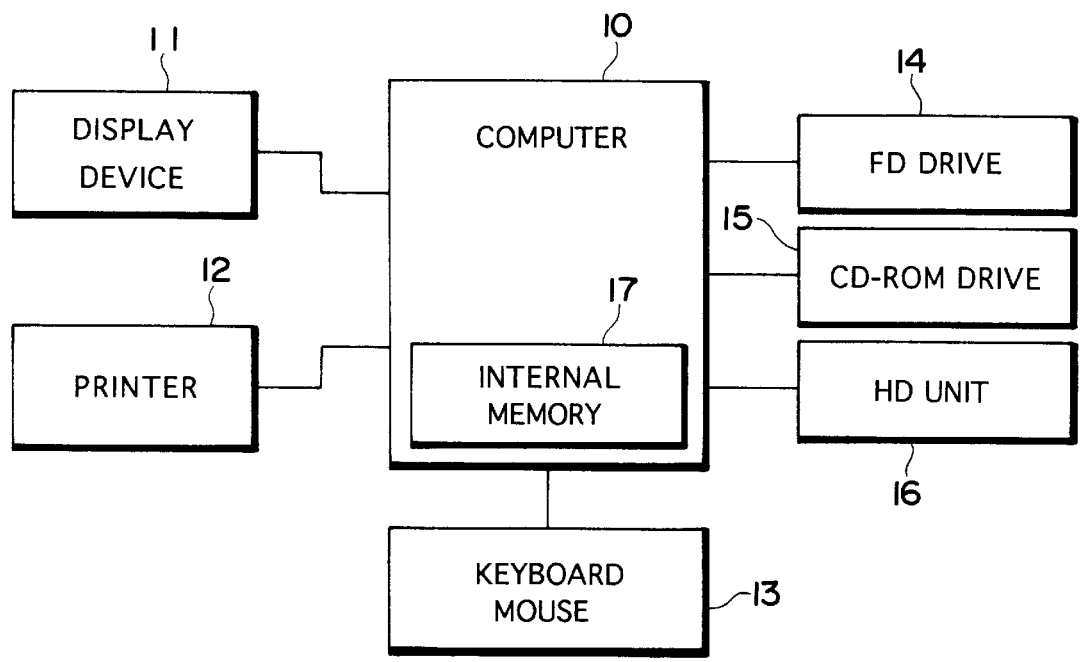
FIG. 5 is a block diagram showing the electrical configuration of the apparatus for analyzing a filament.

FIG. 4 illustrates the appearance of an apparatus for analyzing a linear object, and FIG. 5 illustrates the outline of the electrical configuration thereof.

The apparatus for analyzing a linear object comprises a computer 10. A CRT display device (or a liquid crystal (LC) display panel) 11, a printer 12, and an input device (a keyboard 13A and a mouse 13B) are connected to the computer 10. An FD drive 14, a CD-ROM drive 15, and an HD unit 16 are provided inside the computer 10. The FD drive 14 writes data to an FD 19 and reads out data from the FD 19. The CD-ROM drive 15 reads out data from a CD-ROM 18. The HD unit 16 writes data to a hard disk (not shown) and reads out data from the hard disk. The computer 10 further comprises an internal memory (a semiconductor memory, etc.) 17.

A group of keys for entering data for analyzing the filament 1 is provided in the keyboard 13A.

Programs and data for analyzing the filament 1 are stored in the CD-ROM 18.

(2) Processing for analyzing linear object

Figure 6:
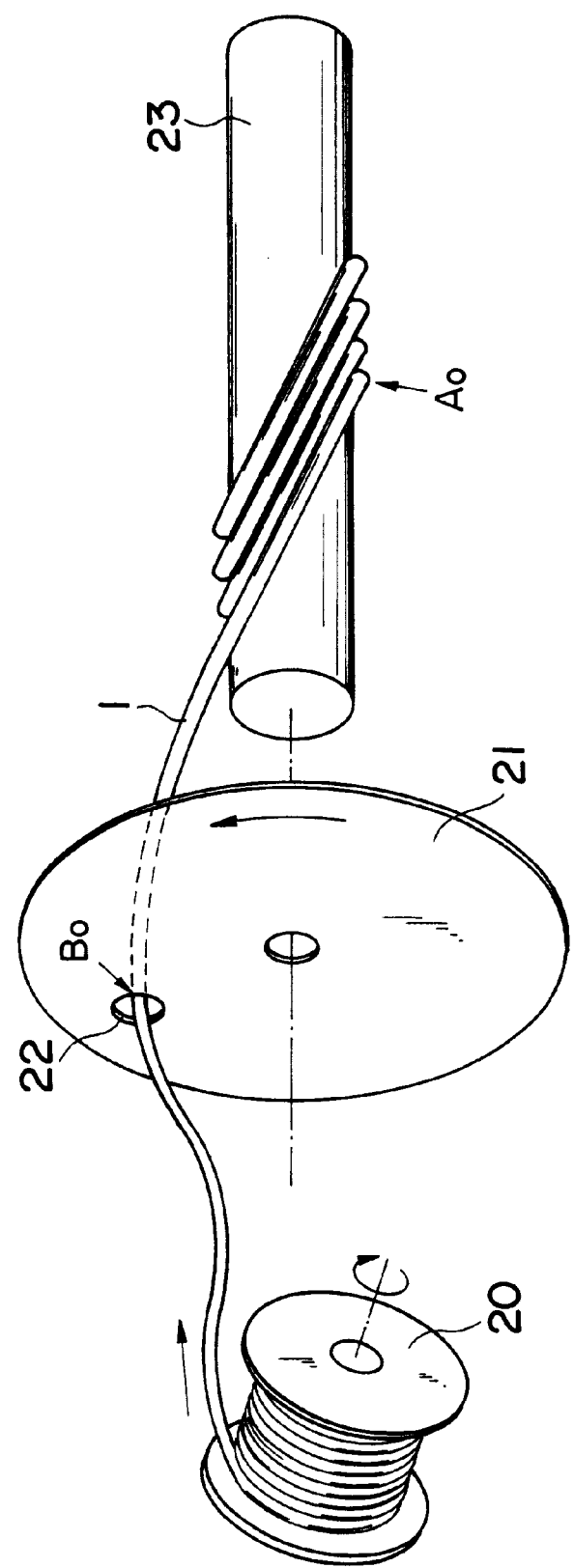
FIG. 6 illustrates a laying forming process of a wire rope.

FIG. 6 is a schematic view showing a part of a laying machine.

The filament 1 is wound around a bobbin 20. One end of the filament 1 is fixed to a forming die 23 through an opening 22 formed in a mirror panel 21.

The mirror panel 21 is rotated, so that the filament 1 wound around the bobbin 20 is pulled out of the bobbin 20, and the filament 1 is wound around the forming die 23, gradually forming a wire rope.

Figure 7:
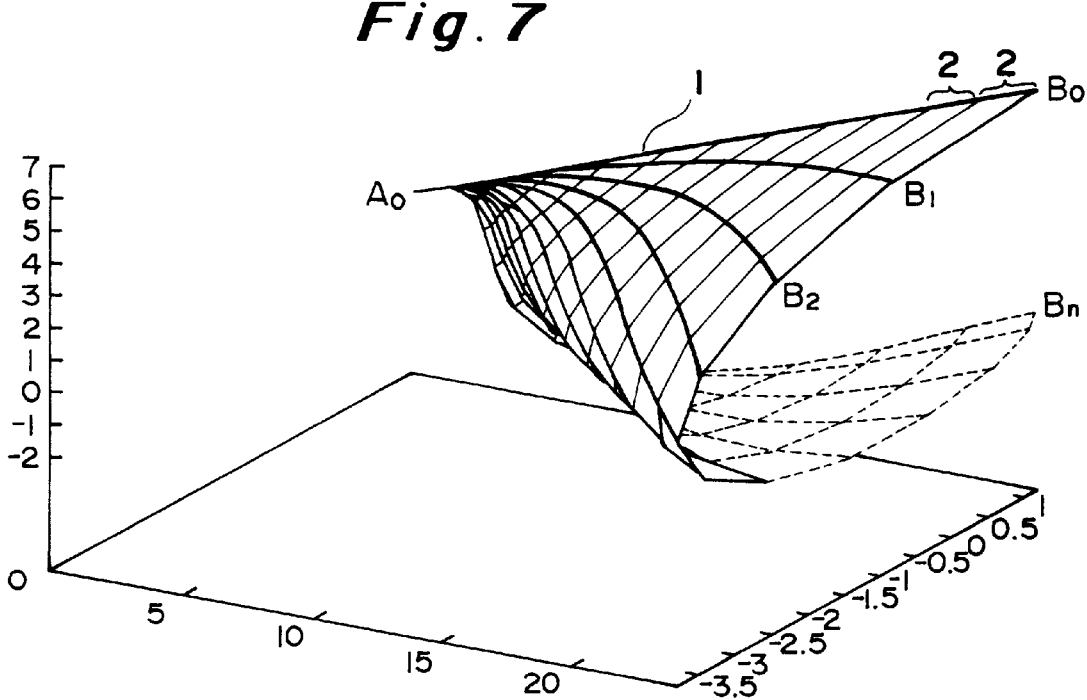
FIG. 7 shows how a filament is deformed.
Figure 8:
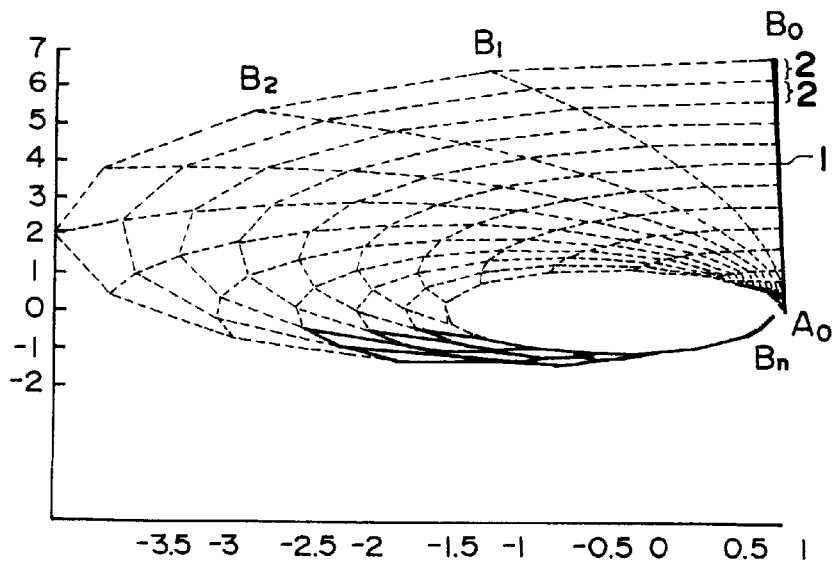
FIG. 8 is a projected view of FIG. 7.

FIGS. 7 and 8 graphically show a laying forming process of a wire rope corresponding to one pitch, where FIG. 7 is a diagram showing three-dimensional representation, and FIG. 8 is a projected view of FIG. 7.

In FIGS. 7 and 8, one section of the filament 1 corresponds to the above-mentioned element 2.

In FIGS. 7 and 8, a portion, at a lower end of the forming die 23 indicated by Point $A_0$, of the filament 1 corresponds to Point $A_0$, and a portion, at a position of the opening 22 of the mirror panel 21 indicated by Point $B_0$, of the filament 1 corresponds to Point $B_0$.

As described above, when the mirror panel 21 is rotated through a predetermined angle, the portion, at the position of the opening 22, of the filament 1 is moved to Point $B_1$. When the mirror panel 21 is further rotated through a predetermined angle, the portion, at the position of the opening 22, of the filament 1 is moved to Point $B_2$. The rotation of the mirror panel 21 for each predetermined angle is repeated, so that the filament 1, corresponding to one pitch, is wound around the forming die 23, as described above. When the filament 1, corresponding to one pitch, is wound around the forming die 23, the portion, at the position of the opening 22, of the filament 1 is moved to Point $B_n$.

Figure 9:
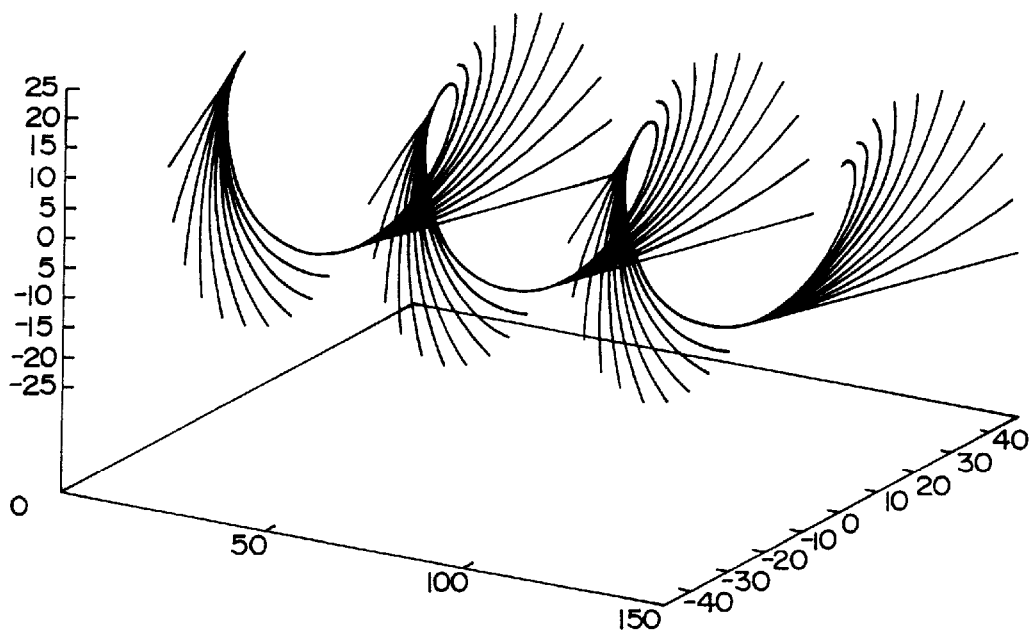
FIG. 9 shows how a filament is deformed.
Figure 10:
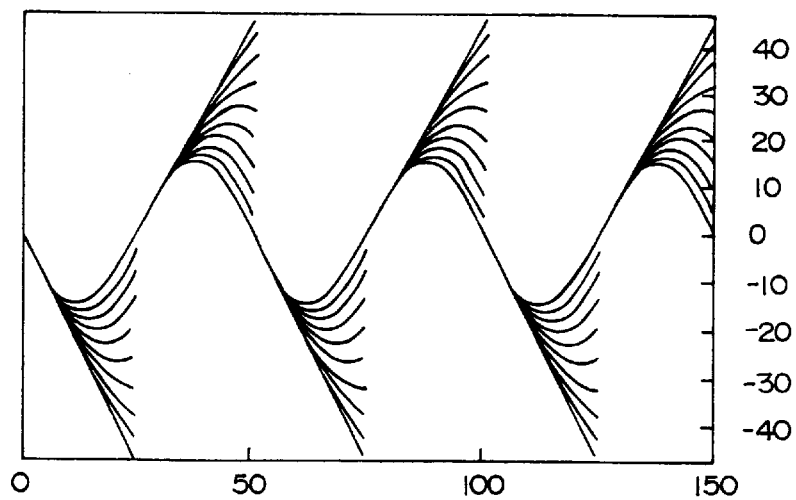
FIG. 10 is a projected view of FIG. 9.

FIGS. 9 and 10 graphically show a laying forming process of a wire rope corresponding to three pitches, where FIG. 9 is a diagram showing three-dimensional representation, and FIG. 10 is a projected view of FIG. 9.

As described with reference to FIGS. 6 to 8, the laying forming process of the wire rope corresponding to one pitch is repeated, thereby forming the wire rope.

When the load applied to the filament 1 for each pitch is changed, analysis corresponding to several pitches is required. If the load applied to the filament 1 for each pitch is not changed, analysis corresponding to one pitch is sufficient.

Figure 11:
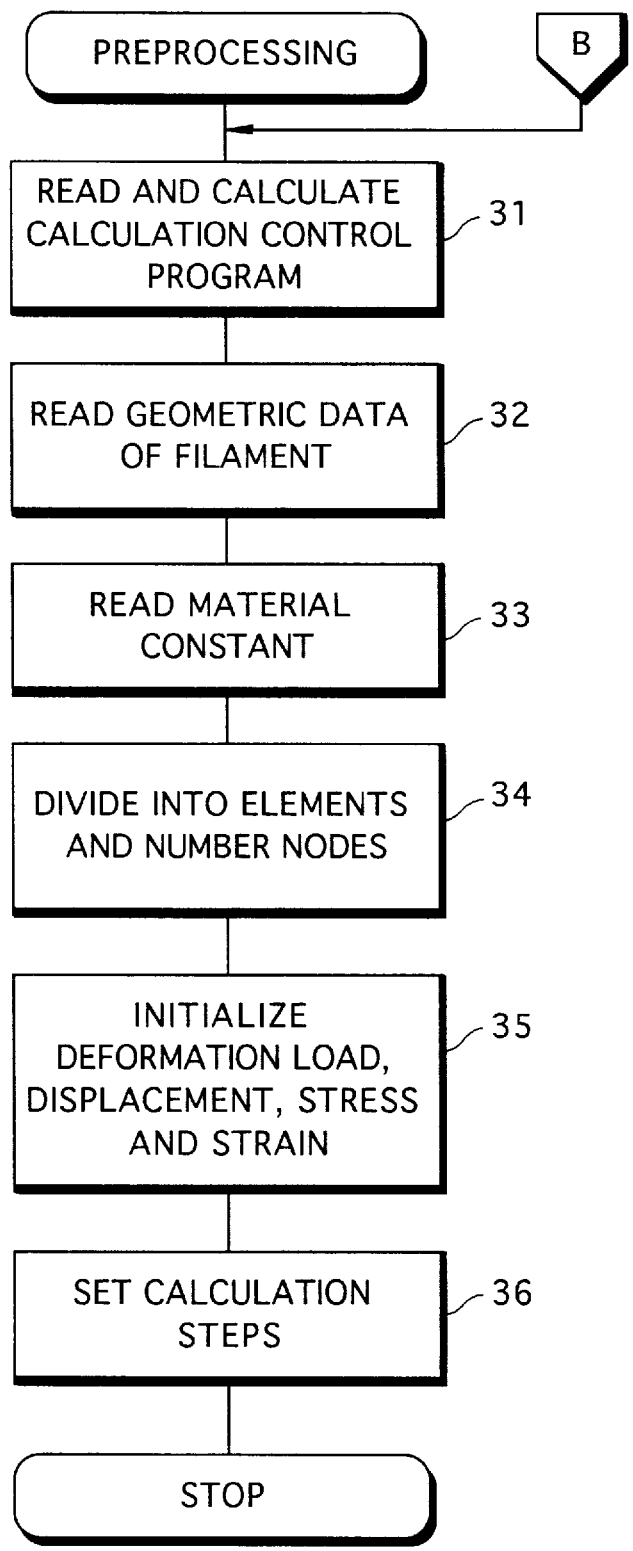
FIGS. 11, 12, and 13 are flow charts showing the procedure for analysis processing of a filament.
Figure 12:
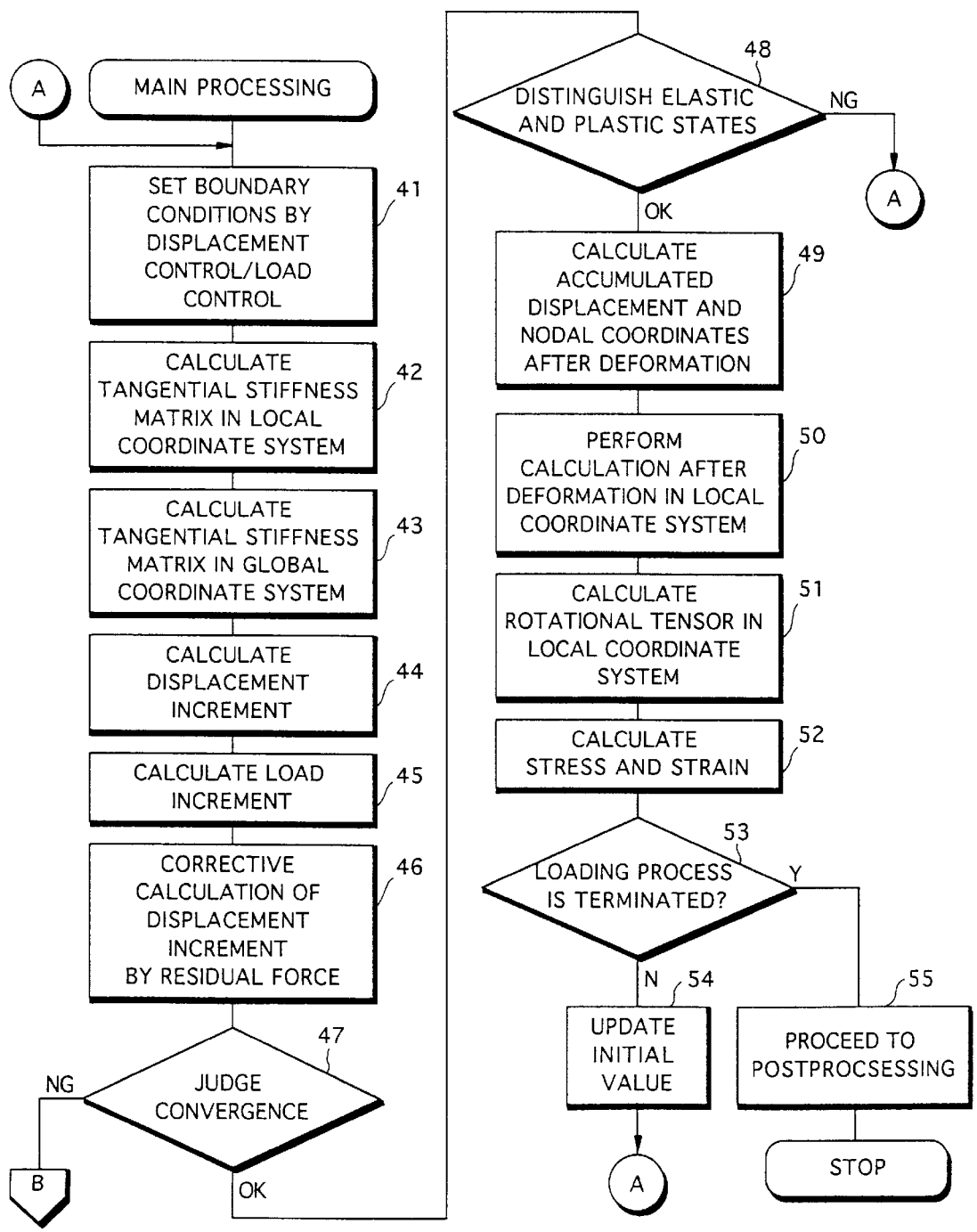
Figure 13:
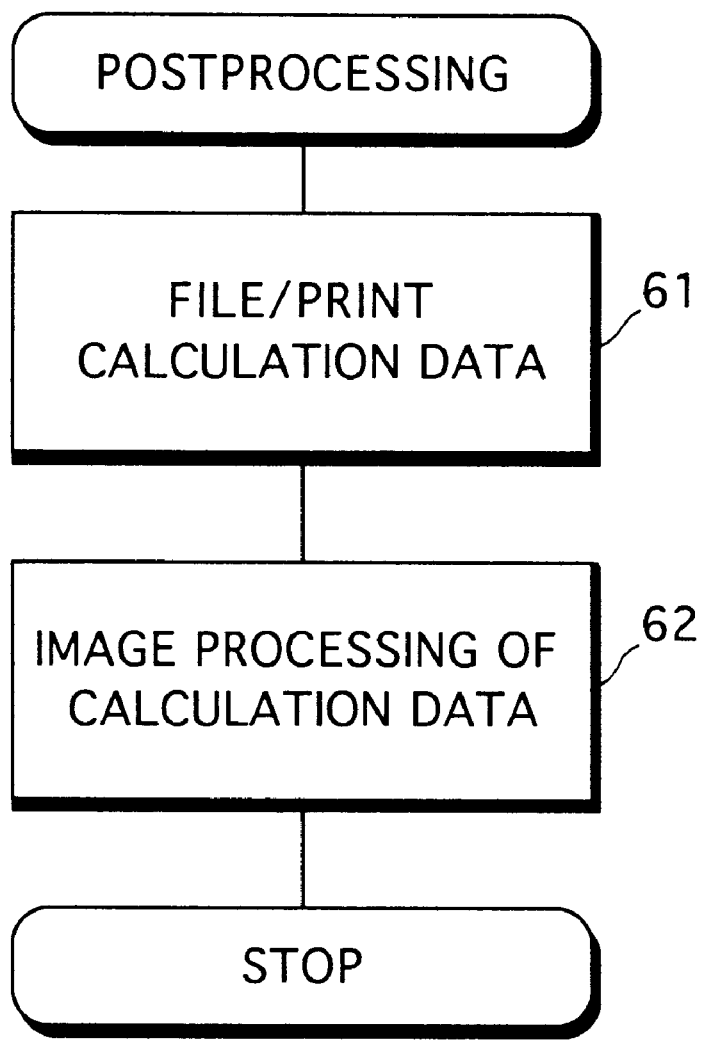

FIGS. 11 to 13 are flow charts showing the procedure for processing for analyzing a wire rope. FIG. 11 shows pre-processing performed before a displacement or a load in each portion of the filament are calculated, FIG. 12 shows processing for actually calculating the displacement or the load in each portion of the filament, and FIG. 13 shows post-processing performed after the displacement or the load is calculated.

Referring to FIG. 11, calculation control parameters are first read and calculated (step 31). Examples of the processing include setting of the number of elements indicating how many elements 2 should be obtained by dividing the filament 1 (the number of elements is determined by an operator), reading of the number of nodes in the element 2, and calculation of the number of degree of freedom, the number of times of repetitive calculation, and so forth.

Geometric data of the filament 1 is then read (step 32). Examples of the geometric data include, in laying the filament 1 to form a wire rope, the diameter of the wire rope, the diameter of a strand, the diameter of the filament (wire) 1, the number of filaments 1, a laying pitch, the direction of lay, and the length of the wire rope.

The material constant of the filament 1 is then read (step 33). Examples of the material constant include a longitudinal elastic constant, a shear modulus of elasticity, a Poisson's ratio, a yield stress, tension in a case where a yield load is applied, and a work-hardening ratio.

Furthermore, the element 2 is divided, and the nodes are numbered (step 34). Serial numbers are assigned to the nodes in the filament 1 by this processing. In the processing, element coordinates and an initial local coordinate system are also set.

A deformation load, a displacement, a stress and a strain are initialized (step 35), and how many times the calculating step should be carried out to terminate the calculation is set (step 36). For example, in the example shown in FIG. 7, the filament 1 is formed into a final shape by carrying out the calculating step n times, to terminate the calculation.

In the foregoing manner, the preprocessing is terminated. When the preprocessing is terminated, the program proceeds to main processing.

The end $B_0$ of the filament 1 shown in FIG. 7 is moved to the position $B_1$ by the first main processing shown in FIG. 12, and the end of the filament 1 moved to the position $B_1$ is moved to the position $B_2$ by the second main processing. The filament 1 is formed into a final shape by repeating the main processing n times, to terminate the main processing.

The target shape of the filament 1 by the first deformation is determined (for example, in the example shown in FIG. 7, displacements and loads at the nodes in the element 2 of the filament 1 are calculated such that the end Bo of the filament 1 moves to the position $B_1$) (step 41, setting of boundary conditions by displacement control/load control of the filament 1).

A tangential stiffness matrix $K_e$ for each element 2 in the local coordinate system is then calculated, as described above, for all the elements 2 (step 42).

When the tangential stiffness matrix $K_e$ for each element 2 in the local coordinate system is calculated, the calculated tangential stiffness matrix $K_e$ is translated into a tangential stiffness matrix $K_T$ for the element 2 in the global coordinate system, as described above (step 43).

When the tangential stiffness matrix $K_e$ for each element 2 in the local coordinate system is translated into the tangential stiffness matrix $K_T$ for the element 2 in the global coordinate system, a global stiffness equation for the filament 1 is calculated, as described, and a displacement increment and a load increment are calculated on the basis of the global stiffness equation (steps 44 and 45).

Since the value of the displacement increment and the value of the load increment which are calculated at the steps 44 and 45 are not theoretically equal to each other, corrective calculation of the displacement increment is performed using a residual force (a difference between a nodal force and an actual external force) such that the values are equal to each other (step 46).

It is judged whether or not a value obtained by the corrective calculation converges (step 47). When the value does not converge, the preprocessing (FIG. 11) and the subsequent processing are performed again, upon changing the number of elements, for example.

When the value obtained by the corrective calculation converges, the elastic and plastic states of the element 2 are distinguished (step 48). The elastic and plastic states are distinguished from the yield load. When too many elements 2 enter a plastic area, the displacement increment is decreased, after which the step 41 and the subsequent steps are carried out again.

How many displacements are produced from the initial shape of the filament 1 is then calculated as an accumulated displacement, and nodal coordinates after the deformation are calculated (step 49).

The positions of the nodes 1 and 3 are calculated from the position of the node 2, and any position therebetween is interpolated, so that the calculation after deformation in local coordinate system is performed (step 50). A rotational tensor T is calculated using a value obtained by the calculation in order to calculate a tangential stiffness equation for each element 2 in the global coordinate system in the subsequent main processing (step 51).

Furthermore, a stress and a strain in an arbitrary portion of the element 2 are calculated on the basis of the displacement increment and the load increment which are calculated at the steps 44 and 45 (step 52).

It is judged whether or not the filament 1 has a final target shape (whether or not a loading process is terminated) (step 53). If the filament 1 does not have the final shape (NO at step 53), a nodal displacement and a nodal load are updated (step 54), after which the processing at the step 41 and the subsequent steps is repeated.

When the filament 1 has the final shape (YES at step 53), the program proceeds to postprocessing (step 55).

Referring to FIG. 13, in the postprocessing, the result of calculation data is stored as a file in the internal memory 17, and is printed by the printer 12 (step 61).

An image representing the state of an internal stress in the laid filament 1 is displayed on the display device 11 on the basis of obtained image data (step 62). The operator can visually recognize the state of an internal load of the filament 1 by viewing the display.

FIG. 14 shows input data in a case where the characteristics of the wire rope which is calculated in laying the filament 1 is obtained using the above-mentioned method of analyzing a liner object.

FIG. 15 shows the coordinate positions of the nodes in the global coordinate system in the elements of the filament 1 obtained by the input data as shown in FIG. 14, and FIG. 16 shows residual stresses produced in the wire rope. Data shown in FIGS. 15 and 16 will be printed (step 61 in FIG. 13).

FIGS. 17*a* to 21*c* illustrate the residual stresses in the wire rope represented by the data obtained using the method of analyzing a linear object in the present embodiment, where FIGS. 17*a*, 18*a*, 19*a*, 20*a* and 21*a* illustrate a state where the inverse ratio is zero, FIGS. 17*b*, 18*b*, 19*b*, 20*b* and 21*b* illustrate a state where the inverse ratio is 0.83, and FIGS. 17*c*, 18*c*, 19*c*, 20*c* and 21*c* illustrate a case where the inverse ratio is 1.0.

Figures 17A, 17B, 17C:
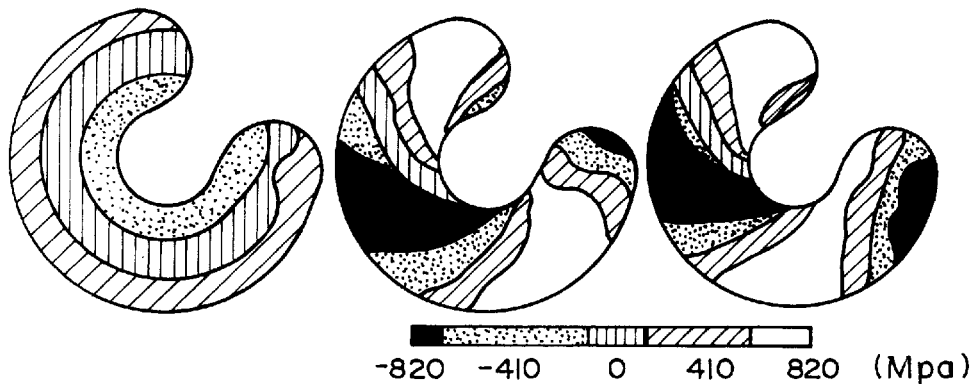
FIGS. 17a to 17c illustrate a residual normal stress produced in each portion of a wire rope when the wire rope is loaded.

FIGS. 17*a*, 17*b* and 17*c* illustrate a residual normal stress produced when the wire rope is in a loaded state and viewed along its length.

Figures 18A, 18B, 18C:
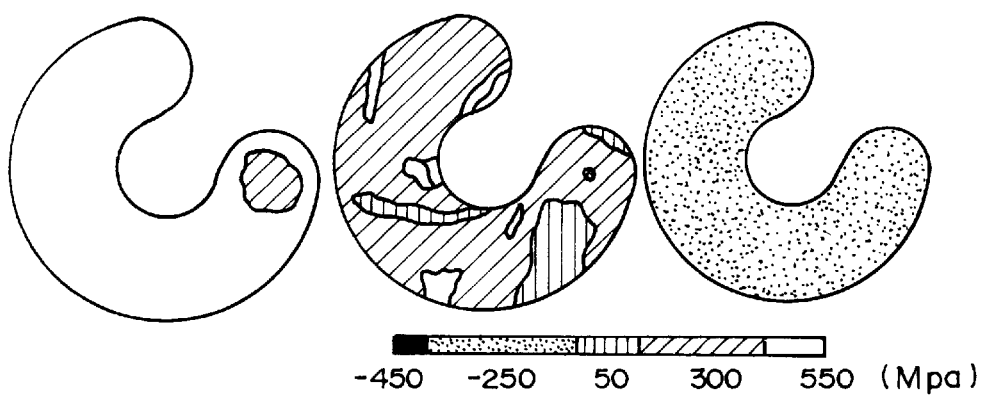
FIGS. 18a to 18c illustrate a residual shear stress produced in each portion of a wire rope when the wire rope is loaded.

FIGS. 18*a*, 18*b* and 18*c* illustrate a residual -shear stress produced when the wire rope is in a loaded state and viewed along its length.

Figures 19A, 19B, 19C:
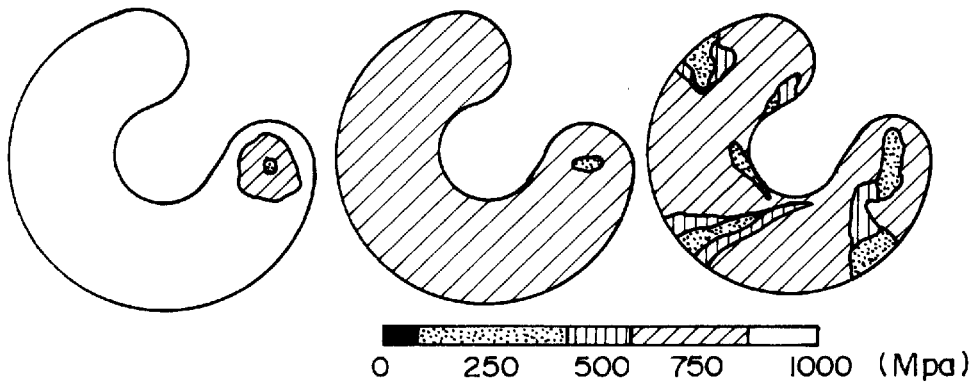
FIGS. 19a to 19c illustrate a residual equivalent stress in a case where a wire rope is unloaded.

Furthermore, FIGS. 19*a*, 19*b* and 19*c* illustrate a residual equivalent stress produced when the wire rope is in a loaded state and viewed along its length.

FIGS. 20*a*, 20*b* and 20*c* illustrate a residual normal stress in a case where the wire rope is unloaded.

FIGS. 21*a*, 21*b* and 21*c* illustrate a residual shear stress in a case where the wire rope is unloaded.

Of FIGS. 20*a* to 21*c*, FIGS. 20*a*, 20*b*, 21*a* and 21*b* respectively illustrate states where the wire rope is viewed from its length, while FIGS. 20*c* and 21*c* respectively illustrate states viewed in a direction different from the direction shown in FIGS. 20a, 20b, 21a and 21b in order to make the state of the residual stress easy to understand.

FIGS. 20a and 20b are illustrated on the basis of the data shown in FIGS. 14 to 16. FIGS. 17a to 21c excluding FIGS. 20a and 20b can be also easily illustrated in the same manner. Data for obtaining FIGS. 17a to 21c excluding FIGS. 20a and 20b are not shown in order to avoid complexity.

What is claimed is:

1. A method of analyzing a linear object, comprising the steps of:

dividing a linear object having a cross-sectional shape which is substantially uniform along its length and having a length long enough in comparison with a diameter of the linear object into a plurality of elements with predetermined spacing along the length;

determining, when the linear object is deformed, a shape after the deformation;

deriving for each of the elements a tangential stiffness equation in a local coordinate system using the element as a basis in the determined shape;

translating the derived tangential stiffness equation for each of the elements in the local coordinate system into a tangential stiffness equation for each of the elements in a global coordinate system using the linear object as a basis;

deriving a global stiffness equation for the whole of the linear object from the tangential stiffness equation for each of the elements in the global coordinate system which is obtained by the translation; and calculating at least one of the displacement and the load of each of the elements on the basis of the derived global stiffness equation for the whole linear object and the shape after the deformation.

2. The method according to claim 1, wherein the translation from the tangential stiffness equation for each of the elements in the local coordinate system into the tangential stiffness equation for each of the elements in the global coordinate system is separately made on rigid-body rotation of the element and torsional deformation and bending deformation of the element.

3. The method according to claim 1, wherein processing for deriving the tangential stiffness equation for each of the elements in the local coordinate system, translating the derived tangential stiffness equation for each of the elements in the local coordinate system into the tangential stiffness equation for each of the elements in the global coordinate system, deriving the global stiffness equation for the whole linear object, and calculating at least one of the displacement and the load is repeated until the linear object has a final shape.

4. The method according to claim 1, wherein at least one of a stress and a strain in each of the elements is calculated on the basis of at least one of the calculated displacement and the calculated load.

5. The method according to claim 1, wherein the center of the element is the origin of the local coordinate system.

6. The method according to claim 1, wherein nodes in the element are both ends and the center on the central axis of the element.

7. An apparatus for analyzing a linear object, comprising:

setting means for performing such setting as to divide a linear object having a cross-sectional shape which is substantially uniform along its length and having a length long enough in comparison with a diameter of the linear object into a plurality of elements with predetermined spacing along the length;

shape determining means for determining, when the linear object is deformed, a shape after the deformation;

stiffness equation deriving means for deriving for each of the elements, which are obtained by the setting in said setting means, a tangential stiffness equation for each of the elements in a local coordinate system using the element as a basis in the shape determined by said shape determining means;

stiffness equation translating means for translating the tangential stiffness equation for each of the elements in the local coordinate system, which is derived by said stiffness equation deriving means, into a tangential stiffness equation for each of the elements in a global coordinate system using the linear object as a basis;

global stiffness equation deriving means for deriving a global stiffness equation for the whole linear object from the tangential stiffness equation for each of the elements in the global coordinate system which is obtained by the translation in said stiffness equation translating means; and calculating means for calculating at least one of the displacement and the load of each of the elements on the basis of said global stiffness equation for the whole linear object which is derived by the global stiffness equation deriving means and the shape determined by said shape determining means.

8. The apparatus according to claim 7, wherein said stiffness equation translating means makes the translation of the tangential stiffness equation for each of the elements in the local coordinate system into the tangential stiffness equation for each of the elements in the global coordinate system separately on rigid-body rotation of the element and torsional deformation and bending deformation of the element.

9. The apparatus according to claim 7, further comprising means for carrying out such control as to repeat processing for deriving the tangential stiffness equation for each of the elements in the local coordinate system by said stiffness equation deriving means, translating the derived tangential stiffness equation for each of the elements in the local coordinate system into the tangential stiffness equation for each of the elements in said global coordinate system by said stiffness equation translating means, deriving the global stiffness equation for the whole linear object by said global stiffness equation deriving means, and calculating at least one of the displacement and the load by said calculating means until the linear object has a final shape.

10. The apparatus according to claim 7, wherein at least one of a stress and a strain in each of the elements is calculated on the basis of at least one of the displacement and the load which are calculated by said calculating means.

11. The apparatus according to claim 7, wherein the center of the element is the origin of the local coordinate system.

12. The method according to claim 7, wherein nodes in the element are both ends and the center on the central axis of the element.

13. A computer readable recording medium having a program stored thereon for calculating, when a linear object having a cross-sectional shape which is substantially uniform along its length and having a length long enough in comparison with a diameter of the linear object is divided into a plurality of elements with predetermined spacing along the length, the displacement of each of the elements, the program controlling a computer so as to:

determine, in a case where the linear object is deformed, a shape after the deformation;

derive for each of the elements a tangential stiffness equation in a local coordinate system using the element as a basis in the determined shape;

translate the derived tangential stiffness equation for each of the elements in the local coordinate system into a tangential stiffness equation for each of the elements in a global coordinate system using the linear object as a basis;

derive a global stiffness equation for the whole linear object from the tangential stiffness equation for each of the elements in the global coordinate system which is obtained by the translation; and calculate at least one of the displacement and the load of each of the elements on the basis of the derived global stiffness equation for the whole linear object and the shape after the deformation.

* * * * *